United States Patent
Zhao et al.

(10) Patent No.: US 10,088,665 B2
(45) Date of Patent: Oct. 2, 2018

(54) OPTICAL SYSTEM OF A STEREO VIDEO ENDOSCOPE WITH LATERAL VIEWING DIRECTION AND STEREO VIDEO ENDOSCOPE WITH LATERAL VIEWING DIRECTION

(71) Applicant: OLYMPUS WINTER & IBE GMBH, Hamburg (DE)

(72) Inventors: Jianxin Zhao, Hamburg (DE); Tsutomu Uzawa, Hidaka (JP)

(73) Assignee: OLYMPUS WINTER & IBE GMBH, Hamburg (DE)

(*) Notice: Subject to any disclaimer, the term of this patent is extended or adjusted under 35 U.S.C. 154(b) by 286 days.

(21) Appl. No.: 15/016,791

(22) Filed: Feb. 5, 2016

(65) Prior Publication Data
US 2016/0154231 A1 Jun. 2, 2016

Related U.S. Application Data

(63) Continuation of application No. PCT/EP2014/001876, filed on Jul. 8, 2014.

(30) Foreign Application Priority Data

Aug. 6, 2013 (DE) .......................... 10 2013 215 422

(51) Int. Cl.
*G02B 23/24* (2006.01)
*H04N 13/243* (2018.01)
(Continued)

(52) U.S. Cl.
CPC ...... *G02B 23/2415* (2013.01); *A61B 1/00096* (2013.01); *A61B 1/00174* (2013.01);
(Continued)

(58) Field of Classification Search
CPC ... A61B 1/04; A61B 1/00096; A61B 1/00193; A61B 1/00174; H04N 13/0242;
(Continued)

(56) References Cited

U.S. PATENT DOCUMENTS 2,239,538 A * 4/1941 Richter .................. G02B 13/02
359/748
2,718,173 A * 9/1955 Hacman .................. G02B 13/00
359/740
(Continued)

FOREIGN PATENT DOCUMENTS

| CN | 1946332 A | 4/2007 |
|---|---|---|
| DE | 4217889 A1 | 12/1993 |

(Continued)

OTHER PUBLICATIONS

Japanese Office Action dated Jul. 4, 2017 in Japanese Patent Application No. 2016-532245.
(Continued)

*Primary Examiner* — Sath V Perungavoor
*Assistant Examiner* — Philip Dang
(74) *Attorney, Agent, or Firm* — Scully, Scott, Murphy & Presser, P.C.

(57) ABSTRACT

An optical system of a stereo video endoscope with lateral viewing direction. The optical system including: a sideways looking distal optical assembly; and a proximal optical assembly. Where the distal optical assembly includes, successively in a direction of light incidence on a common optical axis: an entrance lens configured as a raised negative meniscus, an optical deflection unit; and an exit lens configured as a hollow positive meniscus, Where the distal optical assembly has, at least in sections, a right and a left lens system channel of identical type and arranged parallel to one another, each of the right and left lens system channel
(Continued)

having: a dedicated optical axis, and at least one first lens and an achromatic lens group in the direction of light incidence.

18 Claims, 2 Drawing Sheets

(51) Int. Cl.
*A61B 1/00* (2006.01)
*A61B 1/04* (2006.01)

(52) U.S. Cl.
CPC ............ *A61B 1/00193* (2013.01); *A61B 1/04* (2013.01); *G02B 23/243* (2013.01); *G02B 23/2446* (2013.01); *G02B 23/2453* (2013.01); *H04N 13/243* (2018.05)

(58) Field of Classification Search
CPC ............ G02B 23/2415; G02B 23/2453; G02B 23/2446; G02B 23/243
See application file for complete search history.

(56) References Cited

U.S. PATENT DOCUMENTS

| | | | | |
|---|---|---|---|---|
| 3,059,528 A * | 10/1962 | Allan | ................ | G03B 37/02 348/37 |
| 3,142,236 A * | 7/1964 | Siegmund | ............. | G02B 17/08 359/727 |
| 3,642,351 A * | 2/1972 | Tronnier | ............... | G02B 9/34 359/757 |
| 4,918,583 A * | 4/1990 | Kudo | ................ | G02B 3/005 359/619 |
| 5,005,957 A | 4/1991 | Kanamori et al. | | |
| 5,016,980 A * | 5/1991 | Waldron | ................ | F24J 2/06 359/833 |
| 5,191,203 A | 3/1993 | McKinley | | |
| 5,321,447 A | 6/1994 | Sander et al. | | |
| 5,327,283 A | 7/1994 | Zobel | | |
| 5,588,948 A | 12/1996 | Takahashi et al. | | |
| 5,689,365 A * | 11/1997 | Takahashi | .......... | A61B 1/00179 348/E13.014 |
| 5,743,846 A | 4/1998 | Takahashi et al. | | |
| 5,774,271 A * | 6/1998 | Lagerway | ............... | F21L 14/00 359/649 |
| 5,825,534 A | 10/1998 | Straehle | | |
| 5,850,312 A * | 12/1998 | Kato | ................ | G02B 15/167 359/684 |
| 5,860,912 A | 1/1999 | Chiba | | |
| 6,256,155 B1 | 7/2001 | Nagaoka | | |
| 6,306,082 B1 | 10/2001 | Takahashi et al. | | |
| 6,332,092 B1 * | 12/2001 | Deckert | ............. | G02B 23/2461 600/476 |
| 6,487,440 B2 * | 11/2002 | Deckert | ............. | G02B 23/2407 600/476 |
| 6,618,197 B1 * | 9/2003 | Hayakawa | ............... | G02B 9/60 359/557 |
| 6,894,289 B2 * | 5/2005 | Nilson | ................ | A01K 1/031 250/458.1 |
| 6,995,918 B2 * | 2/2006 | Terasawa | ............. | G02B 13/143 359/649 |
| 7,046,460 B2 * | 5/2006 | Nozawa | .................. | G02B 9/12 359/716 |
| 7,239,454 B2 * | 7/2007 | Kobayashi | ............. | G02B 5/005 355/71 |
| 7,280,283 B1 | 10/2007 | Kasai | | |
| 7,466,418 B2 * | 12/2008 | Nilson | .................. | A01K 1/031 250/458.1 |
| 7,706,682 B2 * | 4/2010 | Keller | .................. | G03B 13/08 348/341 |
| 7,733,497 B2 * | 6/2010 | Yun | ...................... | A61B 5/0059 356/479 |
| 8,003,186 B2 * | 8/2011 | Ishizaki | ................ | C03B 11/08 351/159.01 |
| 8,137,264 B2 | 3/2012 | Moriyama | | |
| 8,197,397 B2 * | 6/2012 | Rovegno | ............ | A61B 1/00193 348/49 |
| 8,284,484 B2 * | 10/2012 | Hoult | ................ | G02B 21/0028 359/385 |
| 2005/0159641 A1 | 7/2005 | Kanai | | |
| 2006/0132931 A1 * | 6/2006 | Epple | .................... | G02B 17/08 359/726 |
| 2007/0041066 A1 * | 2/2007 | Yasuda | .................... | G03H 1/04 359/9 |
| 2012/0245688 A1 * | 9/2012 | Vanaclocha Vanaclocha | ............. | A61F 2/4425 623/17.16 |
| 2013/0057666 A1 * | 3/2013 | Fujii | ...................... | G02B 13/16 348/65 |
| 2013/0078592 A1 * | 3/2013 | McCarthy | ................ | A61C 7/08 433/3 |
| 2013/0176560 A1 * | 7/2013 | Wax | ...................... | G01N 21/49 356/300 |

FOREIGN PATENT DOCUMENTS

| | | | |
|---|---|---|---|
| DE | 19532400 | A1 | 3/1996 |
| DE | 19509885 | B4 | 5/2007 |
| JP | H05-341207 | A | 12/1993 |
| JP | H06-059199 | A | 3/1994 |
| JP | H06-509425 | A | 10/1994 |
| JP | H08-29701 | A | 2/1996 |
| JP | H08-076030 | A | 3/1996 |
| JP | H08-082766 | A | 3/1996 |
| JP | 2000-089105 | A | 3/2000 |
| JP | 2004-226722 | A | 8/2004 |
| JP | 2005-198800 | A | 7/2005 |
| JP | 2006-039259 | A | 2/2006 |
| JP | 2009-251432 | A | 10/2009 |
| WO | 92/19008 | A1 | 10/1992 |

OTHER PUBLICATIONS

International Search Report dated Oct. 1, 2014 issued in PCT/EP2014/001876.
Chinese Office Action dated May 31, 2017 in Chinese Patent Application No. 201480044750.7.
Japanese Office Action dated May 15, 2018 in Japanese Patent Application No. 2016-532245.

\* cited by examiner

OPTICAL SYSTEM OF A STEREO VIDEO ENDOSCOPE WITH LATERAL VIEWING DIRECTION AND STEREO VIDEO ENDOSCOPE WITH LATERAL VIEWING DIRECTION

CROSS-REFERENCE TO RELATED APPLICATION

The present application is a continuation of PCT/EP2014/001876 filed on Jul. 8, 2014, which is based upon and claims the benefit to DE 10 2013 215 422.4 filed on Aug. 6, 2013, the entire contents of each of which are incorporated herein by reference.

BACKGROUND

Field

The present application relates to an optical system of a stereo video endoscope with lateral viewing direction, comprising a sideways looking distal optical assembly and a proximal optical assembly, wherein the distal optical assembly comprises successively in a direction of light incidence an entrance lens, an optical deflection unit and an exit lens, embodied as a hollow positive meniscus, on a common optical axis, wherein the distal optical assembly has at least in sections two right and left lens system channels of identical type and arranged parallel to one another, having in each case a dedicated optical axis, which have in each case in the direction of light incidence at least one first lens and an achromatic lens group, as well as a corresponding stereo video endoscope with lateral viewing direction.

Prior Art

The use of stereoscopic optical systems in endoscopes is currently limited due to the required installation size on straight-ahead looking endoscopes, i.e. on endoscopes with a so-called 0° viewing direction.

A system of a sideways looking stereoscopic endoscope, which has a distal and a proximal optical assembly, is known from U.S. Pat. No. 5,689,365 A. The distal optical assembly is arranged distally behind a tilted entrance window and comprises a plano-convex entrance lens, which sits on a prism deflection unit, in which the tilted optical axis of the system is deflected in the direction of the longitudinal extension of the shaft of the endoscope. A raised positive meniscus lens is arranged at the exit of the prism unit as an exit lens of the distal optical assembly. The proximal optical assembly follows proximally. While the distal optical assembly is connected in a rotationally fixed manner with the jacket tube, the proximal optical assembly is rotatably arranged in the jacket tube in order to enable a change in the viewing direction.

The proximal optical assembly comprises two lens channel systems, namely respectively for the right image and the left image separately, in which respectively one biconvex entrance lens as well as one achromatic group embodied as a doublet are arranged. Two image sensors are connected in a torque-proof manner with this rotatable proximal optical assembly and receive the separate left and right images.

Other different optical systems, which function in a similar manner, are introduced in U.S. Pat. No. 5,689,365 A, wherein for example relay lens sets are also used in order to direct the incident light into the handle of an endoscope and to the image sensors arranged there.

The optical system introduced in U.S. Pat. No. 5,689,365 A realizes a stereo base of less than 1.1 mm with an outer diameter of the endoscope shaft of more than 15 mm. This means that it is not suitable for an endoscopic use due to its diameter and the achievable three-dimensional effect is not large enough. Furthermore, so-called 3D distortions are not corrected sufficiently in the optical system.

With specific reference to FIG. 1 of U.S. Pat. No. 5,689,365, the shows a known stereo video endoscope from the state of the art in a cross-sectional representation. The stereo video endoscope 1 comprises an endoscope shaft 2 and a handle 3. In an outer jacket tube 12, an optical fiber bundle 13 for illuminating the operative field is arranged distal to the endoscope shaft 2, which ends in the handle 3 in a fiber optic connection 4.

In an inner jacket tube (without reference number), a distal optical assembly 14, which has a plano-concave entrance lens 14b, a prism deflection unit 14c and an exit lens 14d embodied as a hollow positive meniscus, is arranged distally behind an entry window 14a. The entrance lens 14b, the deflection unit 14c and the exit lens 14d are connected in a rotationally fixed manner with the shaft 2 or respectively the jacket tube 12.

Subsequent to the distal optical assembly 14, a proximal optical assembly 15 is arranged rotatably within the inner jacket tube, wherein the rotary axis is the central symmetry axis of the endoscope shaft 2. The proximal optical assembly 15 is arranged in a rotatable holder 16 and has two separate lens system channels for a right image and a left image of a stereoscopic image pair. The lens system channels each have, progressing in FIG. 1 from left to right, an aperture 20, a biconvex entrance lens and an achromatic lens group embodied as a doublet. Each of the lens system channels is followed by an image sensor 18.

The entire proximal optical assembly 15 is arranged rotatably in the shaft 2 by means of a coupling element 17, which is connected with the handle 3 and performs rotations of the handle 3 with respect to the shaft 2. A signal cable 19, which ends in an outer signal cable 7 on the end of the handle 3, which can lead for example to an external computer system, is guided through the center of the coupling element 17.

As discussed above, this optical system is affected by stronger 3D distortions, which restrict the usable stereo base.

SUMMARY

In contrast, an object is to provide an optical system of a stereo video endoscope with lateral viewing direction and a corresponding stereo video endoscope with such an optical system, which provides the same or a larger stereo base along with the same or a smaller installation size, wherein 3D distortions are corrected.

This object is solved by an optical system of a stereo video endoscope with lateral viewing direction, comprising a sideways looking distal optical assembly and a proximal optical assembly, wherein the distal optical assembly comprises successively in a direction of light incidence an entrance lens, an optical deflection unit and an exit lens, such as a hollow positive meniscus, on a common optical axis, wherein the distal optical assembly has at least in sections two right and left lens system channels of identical type and arranged parallel to one another, having in each case a dedicated optical axis, which have in each case in the direction of light incidence at least one first lens and an achromatic lens group, in which the entrance lens can be a raised negative meniscus.

In contrast to the optical system according to U.S. Pat. No. 5,689,365 A, the disclosure of which is fully incorporated in the present patent application, the entrance lens is no longer embodied as a plano-convex lens, but rather as a raised negative meniscus lens, which is also called a meniscus in the field of optical imagining. It thus is a convex-concave lens, wherein the curvature radius of the convex lens surface is the same or greater than the curvature radius of the concave lens surface. In the convention of theoretical optics, in which light is always incident from the left, the convex surface in this case is the left surface and the concave surface is the right surface of the entrance lens.

The distal optical unit thus has at the entry a raised negative meniscus and at the exit a hollow positive meniscus. This combination ensures that 3D distortions are reduced or eliminated. It is thus possible to increase the stereo base in the case of a same-sized or smaller installation size since the stereo image is no longer restricted in its 3D effect by 3D distortions.

There can be a ratio $R_l/R_r$ of the curvature radii of the convex surface (61a) and the concave surface (61b) of the entrance lens (61) between 1.0 and 3.0. The abbreviations "l" and "r" here and in the entire application stand for "left" and "right" in the aforementioned convention of theoretical optics. However, this nomenclature should not be confused with the left and right image channels of the stereoscopy.

There can also be a ratio $R_l/R_r$ of the curvature radii of the concave surface (63a) and the convex surface (63b) of the exit lens (63) between 2.0 and 4.0.

There can also be a ratio $FL_A/FL_E$ of the focal lengths of the exit lens (63) and of the entrance lens (63) between −1.55 and −1.75. The abbreviation "FL" indicates the "focal length."

All three of the aforementioned ratios, namely the ratios of the curvature radii of the surfaces of the entrance lens, the surfaces of the exit lens and the focal lengths of the exit and entrance lenses can be in the named ranges. When the corresponding parameters are selected within these ranges, a particularly good 3D distortion compensation is achieved.

The entrance lens together with the deflection unit can be rotatable with respect to the exit lens, wherein an aperture can be arranged in front of the exit lens. In this case, in which only the entrance lens with the deflection unit is rotatable, improved vignetting is achieved.

Alternatively, the entrance lens, the deflection unit and the exit lens can be jointly rotatable, wherein an aperture can be arranged after the exit lens. This alternative improves the stability of the focus position when turning the viewing direction.

The exit lens can be arranged movably in the axial direction for setting a focus position. The axial direction is the direction of the longitudinal extension of the endoscope shaft.

In order to achieve good and stable imaging in the lens system channels with simultaneously low costs, each lens system channel of the proximal optical unit can have a plano-convex lens as the first lens and a triplet as the achromatic lens group.

If the proximal optical unit has one or more optical relay sets, wherein the lens system channels each have one or more optical relay sets or are arranged in front of or behind one or more common optical relay set(s), the separate image information or respectively light bundles of the two lens system channels can be transferred through the endoscope shaft proximally into the handle. Each lens system channel can thereby either have its own relay set or a series of relay sets or a common optical relay set with an overall diameter of the individual lens components of the relay set can be used which is large enough to simultaneously transfer the light beam bundles of both lens system channels. This procedure has the advantage that for example the larger space available in the handle can be used for the use of larger image sensors and/or for further enlargement of the stereo base, i.e. of the distance of the viewing position for the left and right image with respect to each other.

The lens system channels can lead to one or more image sensors, which can be rotationally fixed with respect to the proximal optical assembly and/or with respect to the lens system channels.

The lens system channels can lead, such as via respectively dedicated or common optical relay sets, to a common image sensor, wherein the image sensor receives light from the two lens system channels simultaneously in separated areas of its light-sensitive sensor surface. In this case, it is a large image sensor, which has sufficient space for the non-overlapping areas, which are illuminated by the left channel and the right channel.

Alternatively, the lens system channels lead, via respectively dedicated or common optical relay sets, to a common image sensor, wherein an optical switching element is also included, such as a rotating mirror, a switchable polarizer or a lenticular screen, by means of which the image sensor receives light from the two lens system channels in alternating temporal succession or simultaneously in spatially alternating succession. In this manner, the two light beam bundles of the left and of the right lens system channel are directed to the same surface on the image sensor, wherein the left and right image information is differentiated via the optical switching elements. The optical switching elements listed as examples, namely rotating mirror and switchable polarizer, lead to a temporally alternating selection of the left and right images, while the lenticular screen generates a spatially alternating sequence. A lenticular screen, also called a lenticular lens, is an arrangement of prisms with lens-shaped or triangular cross-sections, which are arranged on a surface distributed in a strip-like or line-like manner. These deflect the light such that successive rows of sensor cells of the image sensor receive light in an alternating manner from the left lens system channel and the right lens system channel.

At least the sideways looking optical elements of the distal optical assembly on one hand and the lens system channels of the proximal optical assembly can be rotatable against each other about a central axis in order to change a viewing direction.

An object is also solved by a stereo video endoscope with lateral viewing direction, comprising a previously described optical system.

Further characteristics will become evident from the description of embodiments together with the claims and the included drawings. Embodiments can fulfill individual characteristics or a combination of several characteristics.

BRIEF DESCRIPTION OF THE DRAWINGS

The embodiments are described below, without restricting the general idea of the invention, based on exemplary embodiments in reference to the drawings, whereby we expressly refer to the drawings with regard to the disclosure of all details that are not explained in greater detail in the text.

In the drawings, the same or similar elements and/or parts are provided with the same reference numbers in order to prevent the item from needing to be reintroduced.

DETAILED DESCRIPTION

Figure 1:
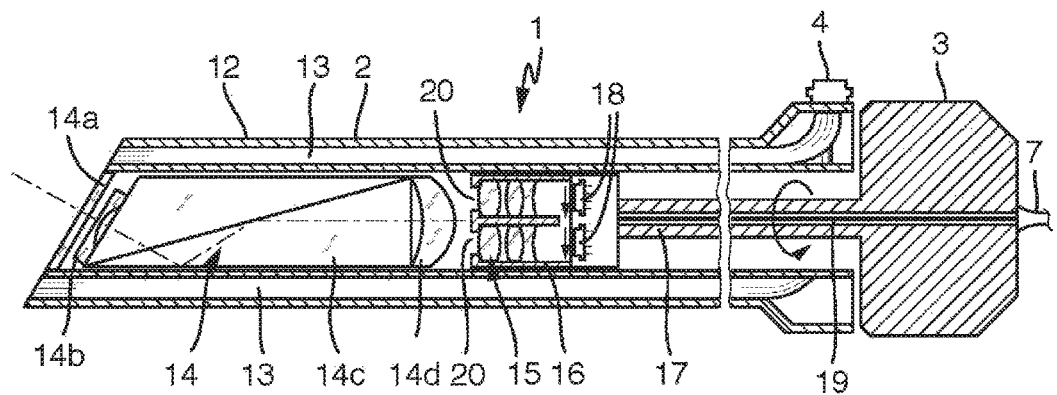
FIG. 1 illustrates a known stereo video endoscope of the prior art with lateral viewing direction in a schematic representation.
Figure 2:
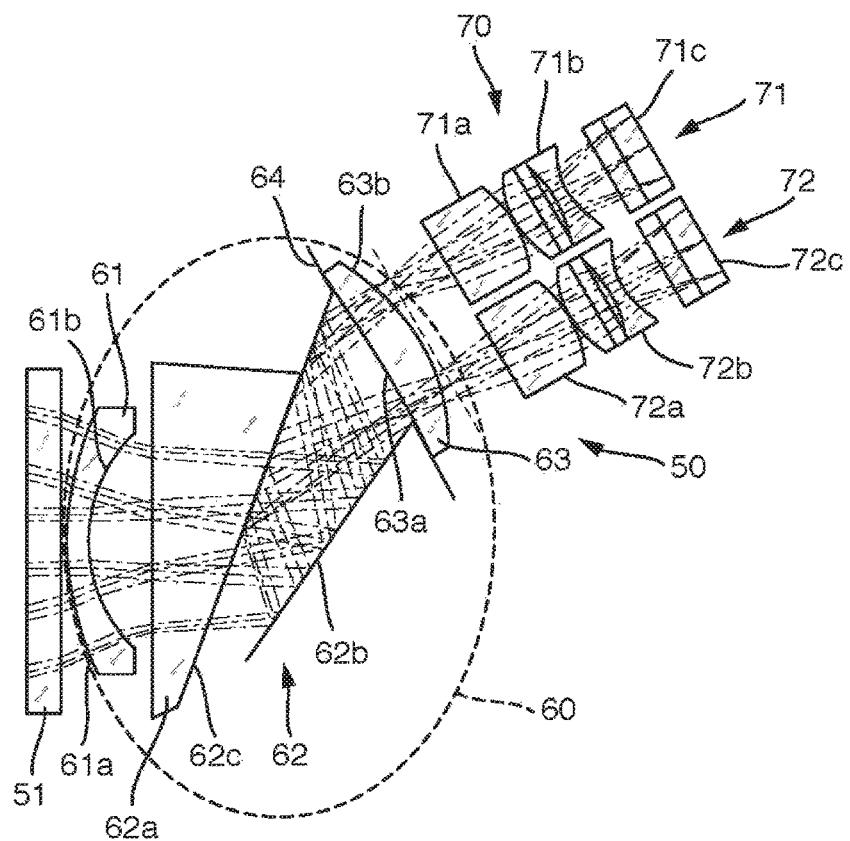
FIG. 2 illustrates an optical system in a schematic representation.

In contrast to FIG. 1, FIG. 2 shows an optical system 50, which has a distal optical assembly 60 and a proximal optical assembly 70 behind an entrance window 51, which corresponds with the entrance window 14a from FIG. 1. The distal optical assembly 60 comprises an entrance 61, which is embodied as a raised negative meniscus, with a convex left surface 61a and a concave right surface 61b, wherein the descriptions left and right in this context are selected with respect to the conventional theoretical optics definition such that light enters on the left and exits on the right. A deflection unit 62 embodied as a prism unit with two partially mirrored or respectively mirrored boundary surfaces 62b, 62c follows, with which the light entering laterally and diagonally is deflected in the direction of the axis of the endoscope shaft. It is a partially mirrored prism 62a and another prism (not shown in greater detail).

Behind the deflection unit 62, an exit lens 63 is arranged behind an aperture 64, which is embodied as a hollow positive meniscus lens, i.e. the left lens surface is concave, the right convex and the curvature radius of the concave lens surface 63a is greater than the curvature radius of the convex lens surface 63b.

After a short distance, the light reaches the first lenses 71a, 72a of the left and right lens system channels 71 and 72 of the proximal optical assembly 70, which are embodied as rod lenses. Achromatic lens groups 71b or respectively 72b connect respectively to these rod lenses 71a, 72a, which are embodied as triplets, of which at least one lens has a high Abbe number. The images sensors 71c, 72c follow.

FIG. 2 shows typical light paths of central and peripheral light bundles. The three light bundles which reach the image sensor 71 correspond with the fifth, third and uppermost bundle (seen from above), which pass through the entrance lens 51, while the bundles which reach the image sensor 72c correspond with the sixth, fourth and second uppermost bundle.

The ratios of the curvature radii of the entrance and exit surfaces of the entrance lens and of the exit lens of the distal optical assembly 60 can all or individually be as follows. The ratio of the curvature radii $R_l/R_r$ of the entrance lens can be 2.03, the ratio $R_l/R_r$ of the exit lens can be 2.63 and the ratio of the focal lengths of the entrance lens to the exit lens can be −1.7. Exemplary curvature radii, optical path lengths, refractive indices and Abbe numbers of the elements of the optical system shown in FIG. 2 are shown in the following table:

TABLE

| R | d | n | v |
|---|---|---|---|
| INF | 50.00 | | |
| INF | 0.58 | 1.77 | 71.8 |
| INF | 0.09 | | |
| 5.101 | 0.36 | 1.81 | 40.9 |

TABLE-continued

| R | d | n | v |
|---|---|---|---|
| 2.511 | 1.03 | | |
| INF | 6.85 | 1.89 | 40.8 |
| INF | 0.11 | | |
| −9.184 | 0.72 | 1.49 | 70.2 |
| −3.490 | 0.14 | | |
| INF | 0.94 | | |
| INF | 1.30 | 1.75 | 49.3 |
| −2.076 | 0.04 | | |
| 1.677 | 0.43 | 1.81 | 40.9 |
| INF | 0.22 | 1.52 | 74.7 |
| INF | 0.07 | | |
| −4.800 | 0.29 | 1.93 | 18.9 |
| 1.437 | 0.70 | | |
| INF | 0.02 | | |
| INF | 0.36 | 1.52 | 64.1 |
| INF | 0.51 | 1.61 | 50.2 |
| INF | (image position) | | |

In the table, the radius and distance data are in millimeters, the refractive index n and the Abbe number v are unitless. A radius labeled "INF" indicates a planar boundary surface. Rows which contain no data for the refractive index n and the Abbe number v indicate air. A lens, such as the entrance lens, comprises two rows of the table. The first row, for example with the radius 5.101, first indicates the left, in this case convex, lens surface. The radius 5.101 mm is positive since this lens surface has a raised curvature. The distance 0.36 corresponds with the thickness of the lens with respect to the optical axis. This is a glass with a high refractive power (n=1.81) and Abbe number v=40.9. In the next row, the curvature radius of the right lens surface is indicated with R=2.511. Since an air gap follows the right lens surface, the distance of 1.03 is specified here as the thickness of the air gap, wherein n and v remain open due to the material being air.

The last three rows of the table indicate that the image sensor is respectively protected by a double layer of glass.

A sideways looking stereo video endoscope with a thickness of 10 mm and a stereo base of 1.3 mm can be realized with the optical system shown in FIG. 2 and in the table.

Figure 3:
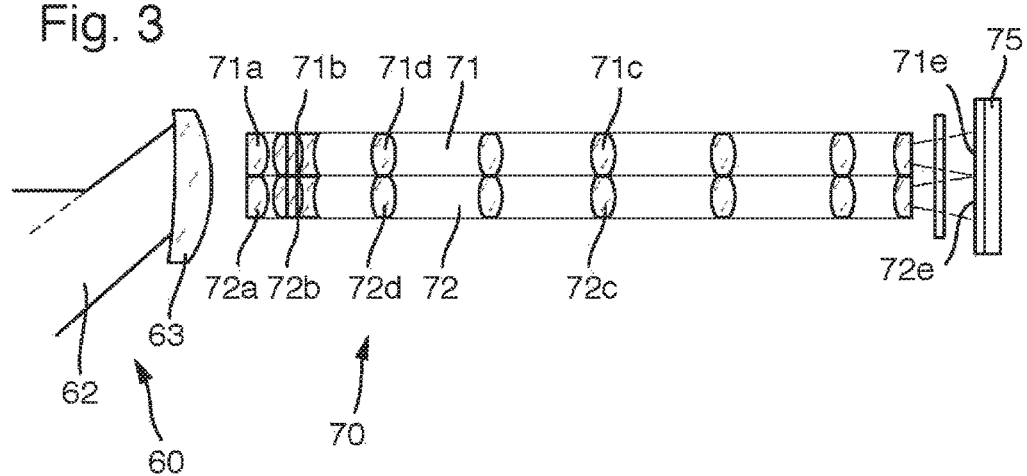
FIG. 3 illustrates details of a further exemplary embodiment of an optical system in a schematic representation.

FIG. 3 shows a detailed view of a further optical system, wherein the deflection unit 62 and the exit lens 63 of the distal optical assembly 60 are shown only in a rudimentary manner. In the exemplary embodiment in FIG. 3, after the first lens 71a, 72a and the triplet achromates 71b, 72b, a series of relay sets 71d, 72d is shown schematically, with which the respective left or respectively right image are forwarded proximally. The relay sets 71d, 72d shown in FIG. 3 are shown symbolically. Actual relay sets are normally embodied as rod lens systems with two or more lenses per relay set. There can be one or more relay sets.

Alternatively and not shown in FIG. 3, a common relay set group or arrangement can also be used instead of respectively dedicated relay sets 71d, 72d of the lens system channels 71 and 72, the diameter of which corresponds with the total diameter of the proximal assembly 70.

The two lens system channels 71, 72 are each terminated in FIG. 3 by means of a diffusion lens, which deflect the respective light bundles to two separate areas 71e, 72e of a common image sensor 75.

Figure 4:
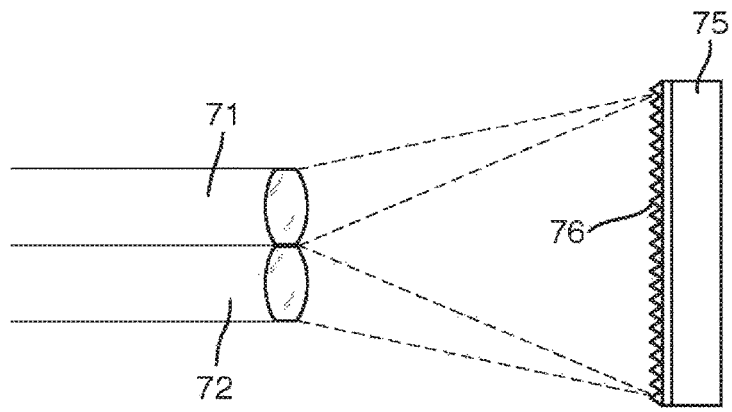
FIG. 4 illustrates details of a further optical system in a schematic representation and FIG. 5 illustrates details of a further optical system in a schematic representation.

FIG. 4 shows an alternative example of the proximal end of the lens system channels 71, 72, wherein the last lenses (without reference numbers) of the lens system channels 71 and 72 direct the respective light beams onto the same surface of the common image sensor 75. On the surface of the image sensor 75, a lenticular screen is arranged in the form of prisms arranged in a lamellar manner, which ensure that light is deflected from the lens system channel 71 and from the lens system channel 72 onto alternating rows of the image sensor 75. Thus, for example, the even rows contain the image of the right channel and the uneven rows the image of the left channel. A different distribution is also possible, for example with a lower spatial frequency.

Figure 5:
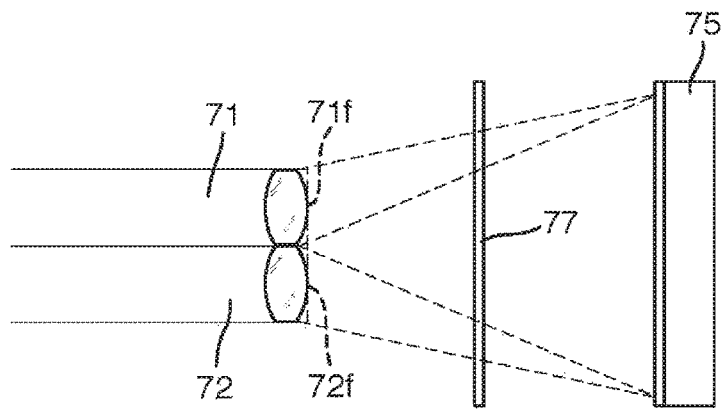

FIG. 5 shows an alternative embodiment, in which the images or respectively the light beams of the left and right lens system channels 71 and 72 are projected in turn onto a common surface on the image sensor 75. The system in FIG. 5 is further developed in that respectively differently polarized polarization filters 71*f*, 72*f* are arranged behind the respective exit of the left and right image channels or respectively lens system channels 71 and 72 and a switchable polarizer 77 is arranged in the path of travel between the lens system channels 71 and 72 and the image sensor 75, which lets through in an alternating manner the polarized light of the left channel and of the right channel. This procedure enables a high optical quality and a large stereo base.

All named characteristics, including those taken from the drawings alone, and individual characteristics, which are disclosed in combination with other characteristics, are considered individually and in combination as essential to the invention. Embodiments can be realized by individual characteristics or a combination of several characteristics.

REFERENCE LIST

1 Stereo video endoscope
2 Endoscope shaft
3 Handle
4 Optical fiber connection
7 Signal cable
12 Jacket tube
13 Optical fiber bundle
14 Distal optical assembly
14*a* Entry window
14*b* Entrance lens
14*c* Deflection unit
14*d* Exit lens
15 Proximal optical assembly
16 Rotatable holder
17 Coupling element
18 Image sensor
19 Signal cable
20 Aperture
50 Optical system
51 Entry window
60 Distal optical assembly
61 Entrance lens
61*a* Convex surface
61*b* Concave surface
62 Deflection unit
62*a* Partially mirrored prism
62*b* Mirrored surface
62*c* Mirrored surface
63 Exit lens
63*a* Concave surface
63*b* Convex surface
64 Aperture
70 Proximal optical assembly
71 Right lens system channel
71*a* First lens
71*b* Achromatic lens group
71*c* Image sensor
71*d* Relay set
71*e* Image area on sensor
71*f* Polarization filter
72 Left lens system channel
72*a* First lens
72*b* Achromatic lens group
72*c* Image sensor
72*d* Relay set
72*e* Image area on sensor
72*f* Polarization filter
75 Common image sensor
76 Lenticular screen
77 Switchable polarizer

What is claimed is:

1. An optical system of a stereo video endoscope with lateral viewing direction, the optical system comprising:
   a sideways looking distal optical assembly; and
   a proximal optical assembly;
   wherein the distal optical assembly comprises, successively in a direction of light incidence on a common optical axis:
      an entrance lens configured as a raised negative meniscus,
      an optical deflection unit; and
      an exit lens configured as a hollow positive meniscus,
   wherein the distal optical assembly has, at least in sections, a right and a left lens system channel of identical type and arranged parallel to one another, each of the right and left lens system channel having:
      a dedicated optical axis, and
      at least one first lens and an achromatic lens group in the direction of light incidence;
   wherein a ratio $FL_A/FL_E$ of focal lengths of the exit lens and of the entrance lens is between −1.55 and −1.75.

2. The optical system according to claim 1, wherein a ratio $R_f/R_r$ of a curvature radii of a convex surface and a concave surface of the entrance lens is between 1.0 and 3.0.

3. The optical system according to claim 1, wherein a ratio $R_f/R_r$ of a curvature radii of a concave surface and a convex surface of the exit lens is between 2.0 and 4.0.

4. The optical system according to claim 1, wherein the entrance lens together with the deflection unit is rotatable with respect to the exit lens.

5. The optical system according to claim 4, further comprising an aperture arranged in front of the exit lens.

6. The optical system according to claim 1, wherein the entrance lens, the deflection unit and the exit lens are jointly rotatable.

7. The optical system according to claim 6, further comprising an aperture arranged after the exit lens.

8. The optical system according to claim 1, wherein the exit lens is arranged movably in the axial direction for adjusting a focus position.

9. The optical system according to claim 1, wherein each lens system channel of the proximal optical unit has a plano-convex lens as the first lens and a triplet as the achromatic lens group.

10. The optical system according to claim 1, wherein the proximal optical unit further comprises one or more optical relay sets, wherein the lens system channels have respectively the one or more optical relay sets arranged in front of or behind one or more common optical relay sets.

11. The optical system according to claim 1, wherein the lens system channels lead to one or more image sensors, the one or more image sensors being rotationally fixed with respect to at least one of the proximal optical assembly and to the right and left lens system channels.

12. The optical system according to claim 1, wherein the right and left lens system channels lead to a common image sensor.

13. The optical system according to claim 12, further comprising one or more dedicated or common optical relay sets, wherein the image sensor receives light from the right and left lens system channels simultaneously in separate areas of a light-sensitive sensor surface.

14. The optical system according to one of claim 1, wherein the right and left lens system channels lead to a common image sensor.

15. The optical system according to claim 14, further comprising one or more dedicated or common optical relay sets, and an optical switching element wherein the image sensor receives light from the right and left lens system channels in alternating temporal succession or simultaneously in spatially alternating succession.

16. The optical system according to claim 15, wherein the optical switching element is selected from a group consisting of a rotating mirror, a switchable polarizer or a lenticular screen.

17. The optical system according to claim 1, wherein at least sideways looking optical elements of the distal optical assembly and the right and left lens system channels of the proximal optical assembly are rotatable against each other about a central axis for changing a viewing direction.

18. A stereo video endoscope with lateral viewing direction, the stereo video endoscope comprising the optical system according to claim 1.

* * * * *